US009889462B2

(12) United States Patent
Ahn et al.

(10) Patent No.: US 9,889,462 B2
(45) Date of Patent: Feb. 13, 2018

(54) ROTATABLE CADDY FOR CATHETERS AND OTHER COILED SURGICAL DEVICES

(71) Applicants: Sam S. Ahn, Los Angeles, CA (US); Travis J. Miller, Dallas, TX (US); Sheena Winwen Chen, Allen, TX (US); Julia Fayanne Chen, Dallas, TX (US); William P. Murphy, Jr., Coral Gables, FL (US)

(72) Inventors: Sam S. Ahn, Los Angeles, CA (US); Travis J. Miller, Dallas, TX (US); Sheena Winwen Chen, Allen, TX (US); Julia Fayanne Chen, Dallas, TX (US); William P. Murphy, Jr., Coral Gables, FL (US)

(73) Assignee: EndoCaddy, LLC, Dallas, TX (US)

( * ) Notice: Subject to any disclaimer, the term of this patent is extended or adjusted under 35 U.S.C. 154(b) by 398 days.

(21) Appl. No.: 14/670,554

(22) Filed: Mar. 27, 2015

(65) Prior Publication Data
US 2015/0273511 A1 Oct. 1, 2015

Related U.S. Application Data

(60) Provisional application No. 61/971,292, filed on Mar. 27, 2014.

(51) Int. Cl.
*B05B 15/02* (2006.01)
*B05C 3/02* (2006.01)
(Continued)

(52) U.S. Cl.
CPC ............ *B05C 3/08* (2013.01); *A61M 25/002* (2013.01); *A61M 25/0111* (2013.01); *A61M 25/0113* (2013.01); *A61M 2025/0046* (2013.01)

(58) Field of Classification Search
CPC ... B05B 13/0228; B05B 13/0257; B05C 3/02; B05C 11/10; B05D 1/002; B05D 1/18
USPC ....................................................... 118/500
See application file for complete search history.

(56) References Cited

U.S. PATENT DOCUMENTS 5,125,416 A * 6/1992 Phillips ............... A61M 25/002
206/364
5,564,589 A * 10/1996 Fu ........................ A47J 27/002
220/573.1
(Continued)

*Primary Examiner* — Cachet I Sellman
(74) *Attorney, Agent, or Firm* — Snyder, Clark, Lesch & Chung, LLP

(57) ABSTRACT

A device comprises a cylinder and a tank. The cylinder includes a first disc and a second disc, multiple struts arranged orthogonally between the first disc and the second disc, and a plurality of walls, parallel to the first disc and the second disc. The struts generally form a circumference with spaces between each of the struts along the circumference; the walls extend through the space between the struts and beyond the circumference of the struts; and the walls form a plurality of tracks around the circumference of the struts. An axle extends orthogonally between the first disc and the second disc, and at least a portion of the cylinder rotates about the axle. The tank includes a basin to hold a liquid solution. When a catheter is wound around the cylinder, the rotation of the cylinder causes the catheter to be coated in the liquid solution from the basin.

18 Claims, 9 Drawing Sheets

(51) Int. Cl.
*B05C 3/08* (2006.01)
*A61M 25/00* (2006.01)
*A61M 25/01* (2006.01)

(56) References Cited

U.S. PATENT DOCUMENTS

| | | | | |
|---|---|---|---|---|
| 5,738,213 A * | 4/1998 | Whiting | ............ | A61M 25/002 206/210 |
| 6,056,226 A * | 5/2000 | Green | ................ | B65H 75/364 191/12.2 R |
| 6,569,106 B1 * | 5/2003 | Ullman | ................ | A61M 25/09 600/585 |
| 6,691,946 B2 * | 2/2004 | Dannecker | .......... | A61M 25/002 242/400.1 |
| 6,802,323 B1 * | 10/2004 | Truwit | ................ | A61M 25/002 134/117 |
| 6,902,057 B2 * | 6/2005 | Duffy | ................ | A61M 25/002 206/364 |
| 8,556,884 B2 * | 10/2013 | Hong | ................ | A61M 25/0017 242/159 |
| 2006/0186256 A1 * | 8/2006 | Mogensen | .......... | A61M 5/1418 242/405.1 |
| 2006/0260968 A1 * | 11/2006 | Mayda, II | ........... | A61M 25/002 206/438 |
| 2008/0017745 A1 * | 1/2008 | Laga | .................... | B65H 75/406 242/395 |
| 2012/0312703 A1 * | 12/2012 | Koellhofer | .......... | A61M 25/002 206/210 |
| 2014/0374295 A1 * | 12/2014 | Lessne | ................ | B65D 85/671 206/364 |

* cited by examiner

ROTATABLE CADDY FOR CATHETERS AND OTHER COILED SURGICAL DEVICES

CROSS-REFERENCE TO RELATED APPLICATION

This application claims priority under 35 U.S.C. § 119, based on U.S. Provisional Application No. 61/971,292, filed Mar. 27, 2014, the disclosure of which is hereby incorporated by reference.

BACKGROUND OF THE INVENTION

Endovascular procedures have become the preferred method of intervention for patients with vascular and cardiovascular disease. These procedures allow lower complications rates and quicker recovery times because instead of making a large incision, only a small puncture, typically through the groin, is required for access. Guidewires, catheters, and interventional devices such as balloons and stents are then threaded through this puncture and guided through different blood vessels to access and treat the patient.

Guidewires are used to direct a catheter to an identified site within a cardiovascular or peripheral vascular system of a patient for the purpose of diagnosis and/or treatment. Catheters are used for administration of fluid, such a saline, contrast, or therapeutic agents, at the identified site. The guidewire is typically placed into a blood vessel of the patient and is directed by a medical practitioner to the identified site of the patient's body. A catheter is then advanced over the guidewire until the functional structure of the catheter is located in proximity of the identified site. Used guidewires or catheters have conventionally been coiled up manually and held down with wet towels on an operating table, thrown into a water basin, or simply placed on the table or floor.

DETAILED DESCRIPTION OF THE PREFERRED EMBODIMENTS

The following detailed description refers to the accompanying drawings. The same reference numbers in different drawings may identify the same or similar elements.

The present invention relates to a rotatable holder for the storage and retrieval of coiled wires, catheters, and the like during endovascular procedures. More specifically, the present invention is directed to a rotatable holder for storage and retrieval of coiled medical guidewires (or simply "wires") and catheters, wherein the rotatable holder facilitates the storage and extraction of the coiled guidewires and catheters from the holder.

In order to navigate to lesions or other areas requiring medical attention in all parts of the body, numerous devices of varying quality and lengths must be used within one procedure. For example, to treat the farthest-most vessel in the lower extremity, an introducer guidewire, a stiff wire, a glide-wire, balloons of varying sizes, one or more catheters with varying tips, and possibly a stent might all be used in one procedure. Each of these items may be at least 45 centimeters (about 18 inches) if not 300 centimeters (about 118 inches) in length; furthermore, newly developed wires and catheters will only become longer in the near future, as different access points (apart from the groin) are beginning to be used. These items are typically kept sterile by manually winding each one into a circle and holding down the ends with the weight of a wet gauze. At times, these items are rethreaded back in their original housing. An additional complication is that after being taken out of their original packaging, these items often look very similar, and the scrub technician is responsible for organizing, tracking, and keeping these items sterile throughout the procedure. This can prove to be a difficult task, especially during complicated procedures that require a high number of disposable endovascular devices. Thus, there remains a need for a storage device that provides an efficient way to organize and manage multiple items in a surgical environment.

Figure 1:
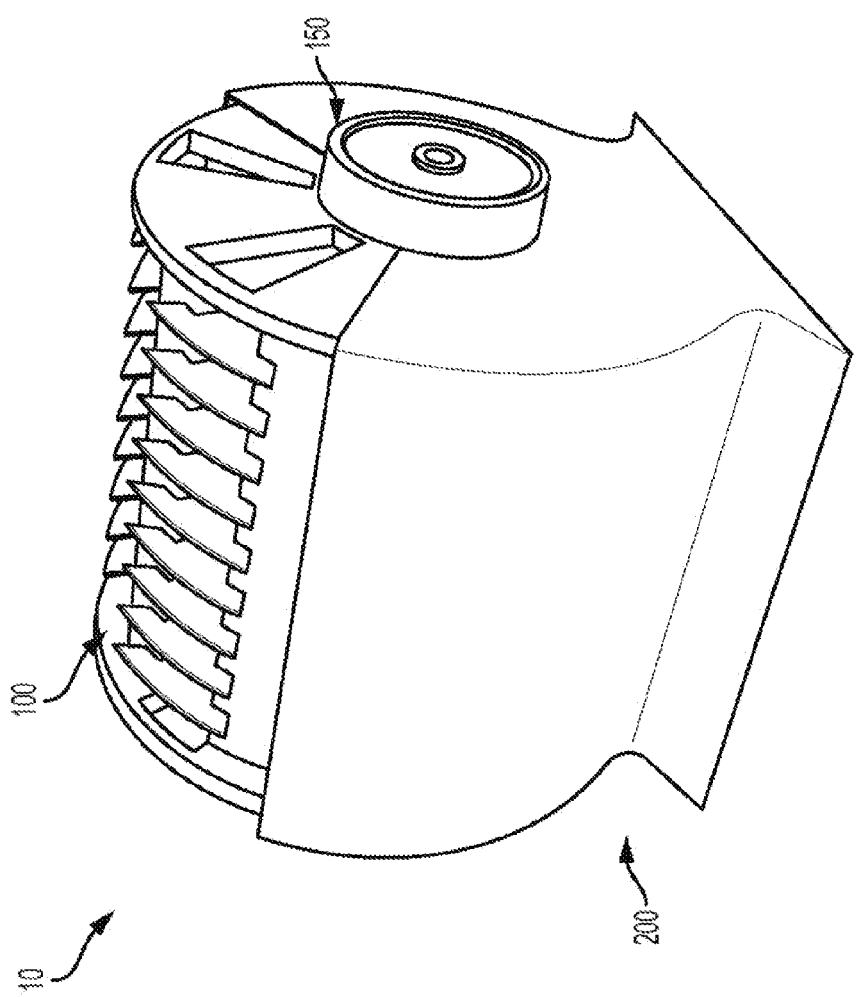
FIG. 1 is an isometric view of a storage device for catheters and wires according to an implementation described herein.
Figure 2:
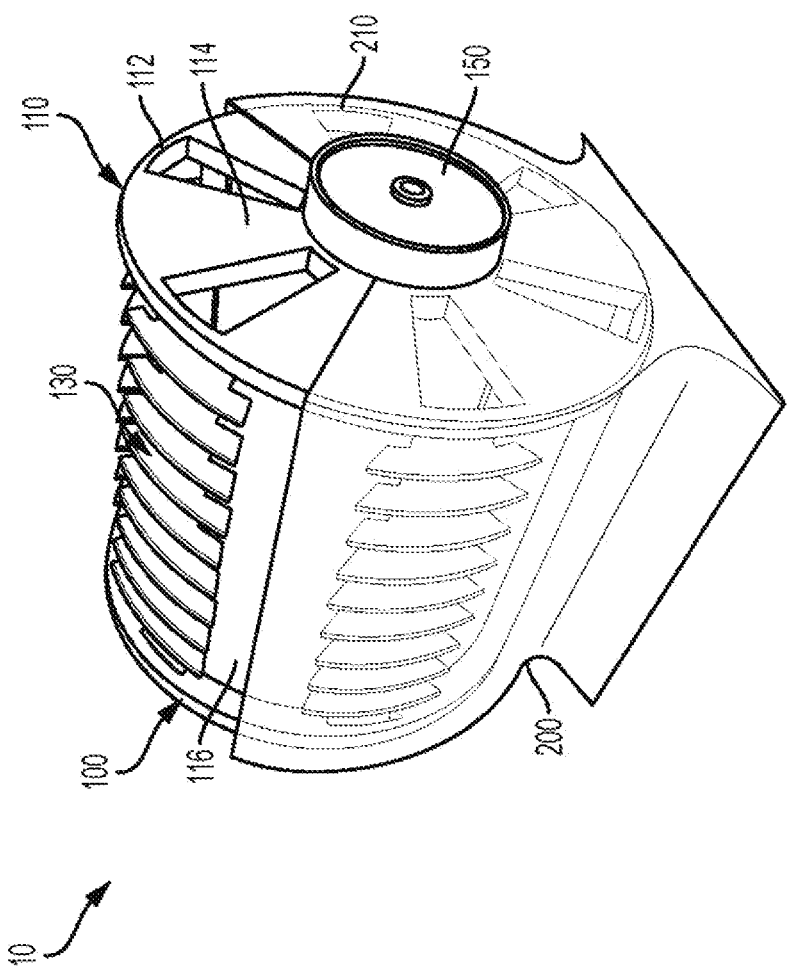
FIG. 2 is another isometric view of the storage device of FIG. 1.
Figure 3:
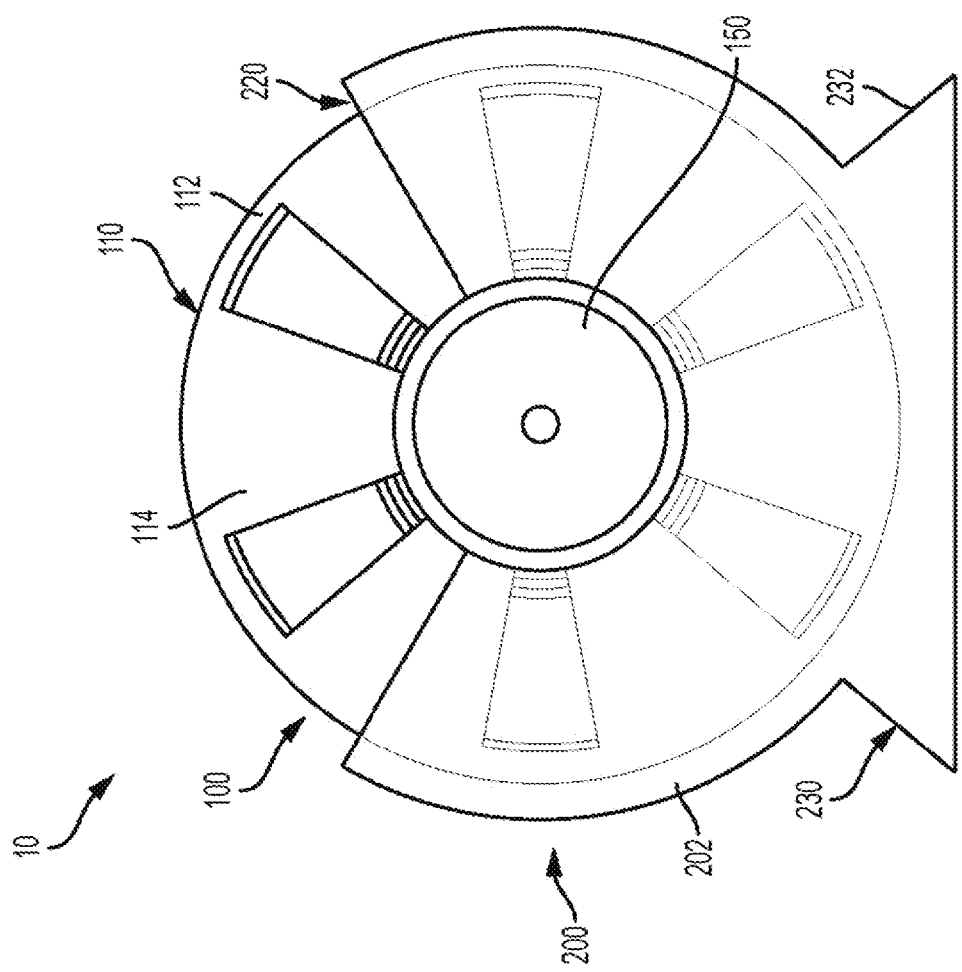
FIG. 3 is an end view of the storage device of FIG. 1.
Figure 4:
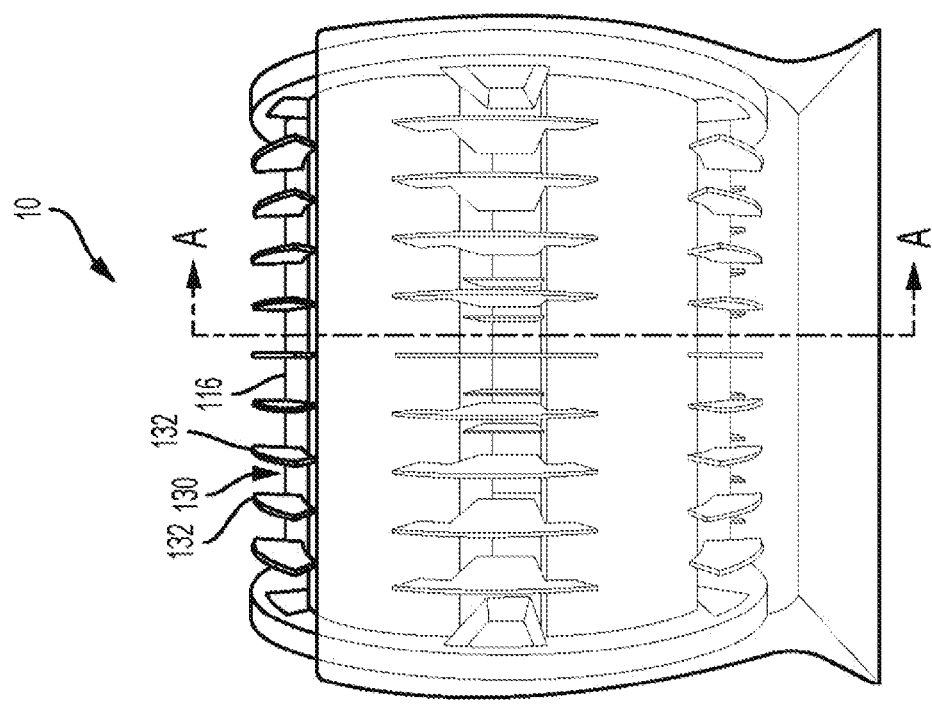
FIG. 4 is a front perspective view of the storage device of FIG. 1.
Figure 5:
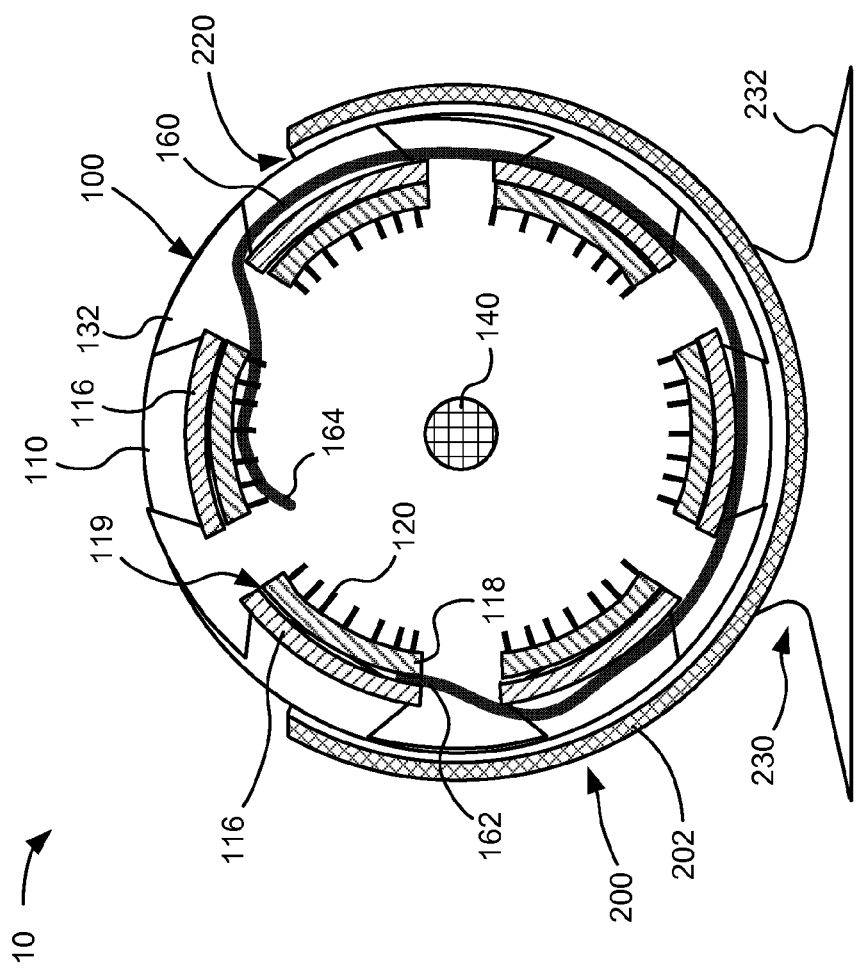
FIG. 5 is a simplified cross-sectional end view of the storage device of FIG. 1, with a catheter or wire inserted.
Figure 6:
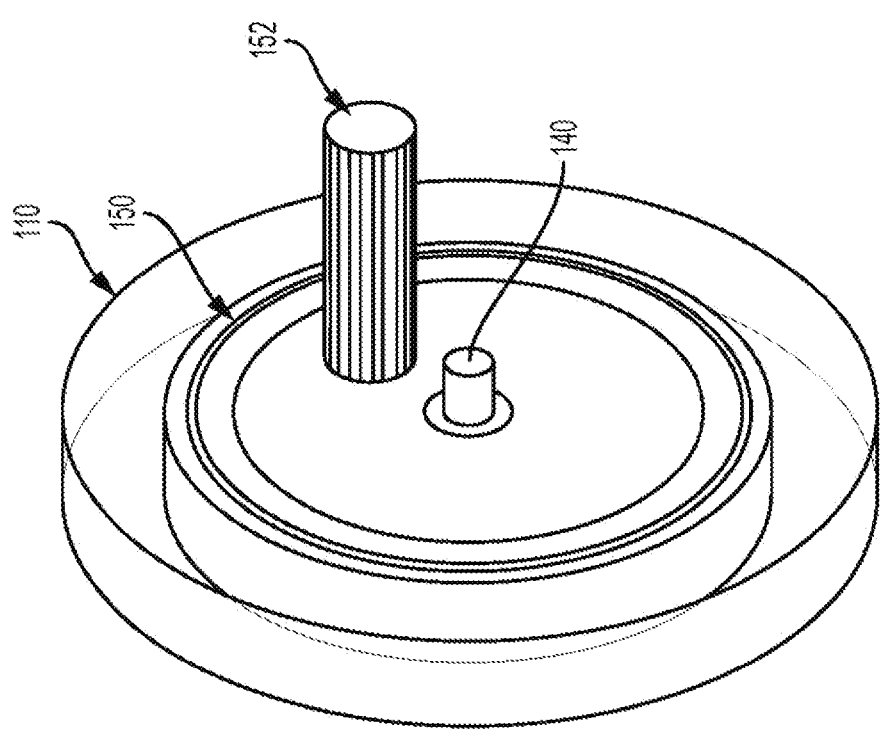
FIG. 6 is an isometric view of a disc and a crank of the storage device of FIG. 1, according to an alternate implementation.

FIGS. 1-6 provide diagrams of exemplary views of a storage device 10 (also referred to herein as a "caddy") according to implementations described herein. More particularly, FIGS. 1 and 2 are isometric views of storage device 10. FIGS. 3 and 4 are an end view and a front perspective view, respectively, of storage device 10. FIG. 5 is a simplified cross-sectional end view, taken along section A-A of FIG. 4, of storage device 10 and shown with a catheter/wire inserted. FIG. 6 is an isometric view of a disc and a crank of storage device 10, according to an alternate implementation.

Referring collectively to FIGS. 1-6, a storage device 10 includes a substantially hollow cylinder 100 oriented lengthwise and contained within a tank 200. Two circular, discs 110 may be attached at opposite ends of cylinder 100. Each of discs 110 may include an outer rim 112 with supports 114. Multiple equally-spaced struts 116 may connect discs 110, forming the length of cylinder 100. Discs 110 and struts 116 may generally be made from a relatively light, rigid material, such as plastic. Immediately beneath each strut 116 lies a malleable layer 118 (FIG. 5) of, for example, spongy foam with dimensions similar to strut 116. Malleable layer 118 is not, however, continuously tightly adhered to strut 116. Potential space 119 between strut 116 and malleable layer 118, created by portions of malleable layer 118 that are not tightly adhered to strut 116, serves as an insertion point for wires (described below). An interior layer 120, which lies beneath strut 116 and malleable layer 118, includes a dense network of bristles projecting toward the center of the cylinder (shown in FIG. 5).

Each strut 116 interrupts a series of equally-spaced tracks 130 (referred to herein collectively as "tracks 130" and individually as "track 130"), each of which runs parallel to rims 112 of discs 110. Each track 130 is formed by raised walls 132 which extend between struts 116 and parallel to discs 110. Walls 132 may be formed, for example, from a rigid plastic or stiff foam material. An axle 140 connecting discs 110 may run through the center of the cylinder 100 and may extend through holes in the center of each disc 110 to the exterior of cylinder 100. In one implementation, discs 110 may be securely mounted to tank 200, allowing for rotation of the interior components of the cylinder 100 (including, e.g., struts 116, malleable layers 118, interior layers 120, and raised walls 132) while the discs 110 (and the device 10 as a whole) remain stationary. In another implementation, discs 110 may be secured to axle 140 and may rotate with other components of cylinder 100, relative to the stationary tank 200.

In still another implementation, tracks 130 may be configured to rotate around axle 140 independently of each other. In this implementation (not shown), each of struts 116 would be separated into discontinuous segments corresponding to a width of each track 130. Each discontinuous segment of strut 116 in a particular track 130 may be secured, for example, to one of walls 132 to permit the wall 132 and the discontinuous segments of struts 116 to rotate around axle 140 (e.g., without turning axle 140). Thus, items 160 in separate tracks 130 may be rotated independently from each other using, for example, a finger to rotate a particular track 130/wall 132. In still another implementation, a locking mechanism (see, e.g., locking mechanism 182 of FIG. 8) may be included for each track 130 to prevent undesired rotation of adjacent tracks 130 when one track 130 is rotated.

Axle 140 of cylinder 100 may rest in a notched recess (not visible in figures) at each end 210 of tank 200. Tank 200 may form a basin 202 to hold a liquid, such as heparinized saline. Tank 200 may include an opening 220 on the top to allow access to cylinder 100 to store and remove items 160, and to introduce the liquid into basin 202.

In one implementation, axle 140 may extend beyond ends 210 of tank 200 to receive a crank 150. Crank 150 may be included at either or both ends 210. Crank 150 can be rotated by the user to cause rotation of axle 140 (and, correspondingly, at least struts 116, malleable layers 118, interior layers 120, and raised walls 132). In one implementation, crank 150 may generally be in the form of a wheel or knob. In another implementation, as shown in FIG. 6, crank 150 may include an additional handle 152 that can be used by a technician to cause rotation of axle 140.

Tank 200 will also allow free rotation of cylinder 100 (e.g., via use of crank 150) such that at least a portion of cylinder 100 can rotate through the liquid in basin 202. The liquid in tank 200 may serve at least two purposes: rotation of the disk device through the saline in basin 202 will moisten stored devices 160, and the saline will also serve to weigh down storage device 10 and stabilize it on a surface (such as a surgical end table). Tank 200 may include a base 230 with extensions 232 extending generally along the length of tank 200. Base 230 may generally be configured to support tank 200 and cylinder 100 and prevent tipping during insertion and/or extraction of items 160 from storage device 10. In one implementation, base 230 may generally be hollow and in fluid communication with basin 202 such that liquid from basin 202 may fill an interior of base 230 to further stabilize storage device 10.

In one implementation, all or a portion of tank 200 may be transparent or semi-transparent so as to permit a technician to see liquid levels and coiled items 160 within basin 202. Tank 200 generally may be made from a relatively light, rigid material that is water resistant, such as plastic.

In practice, one or more items 160 for a surgical procedure may be stored in, removed from, and replace in storage device 10 during a surgical procedure. To prime device 10, the blunt end 162 of an item 160, such as an endovascular wire or catheter, can be inserted into any of the potential spaces 119 created between struts 116 and malleable layer 118. After an item 160 to be stored has been primed, rotation of the cylinder 100 via one of the cranks 150 on the exterior side of discs 110 can reel item 160 onto an outer surface of the wheel, as shown in FIG. 5. Raised walls 132, running between struts 116, will guide item 160 on a track 130 along a circumference of cylinder 100 and provide separation between tracks 130 for storage of multiple items 160. In FIG. 5, a short length of item 160 is shown reeled over several struts 116 along the circumference of cylinder 100 for simplicity. In practice, a single item 160 may be wound for several revolutions around the circumference of cylinder 100.

After item 160 has been reeled onto cylinder 100, a free end 164 of item 160 may be passed through an opening between struts 116 and forced into the dense network of bristles in interior layer 120. For example, a technician may insert a finger through the opening between struts 116 and push end 164 upwards against interior layer 120. The tendency for item 160 to unwind may continue to push the free end 164 of item 160 against the network of bristles in interior layer 120. The bristles of interior layer 120 may stabilize item 160 against the inner surface of cylinder 100 so that both ends of item 160 can be secure. With item 160 secure, additional items 160 (e.g., other wires and catheters, not shown, that may be relevant to the same medical procedure) may be added to the storage device 10 in a similar manner. A limitation on the number of items 160 that may be stored may generally correspond to the number of tracks 130 provided in storage device 10. In one implementation, ten sections of raised walls 132 (along with discs 110) may form eleven tracks 130 for storage device 10. However, in some instances, multiple items 160 may be stored in the same track 130 of storage device 10.

Using space 119 between malleable layer 118 and struts 116 to hold end 162 of item 160 adds versatility to the use of storage device 10. While each track 130 can be designed with the same configuration, each track 130 can be used to hold items 160 of different diameters (such as catheters or wires) securely. In other implementations, the spacing of walls 132 may vary axially along cylinder 100 to provide tracks with different widths.

According to implementations described herein, the hollow shape of cylinder 100, with discs 110 connected by struts 116, permits storage of a portion (e.g., end 164) of item 160 inside cylinder 100. As item 160 is wrapped around cylinder 100, the tendency of the item 160 will be to flex out and resist being stored in a compact circular shape. By storing end 164 of item 160 inside of cylinder 100, when the configuration of item 160 causes end 164 to attempt to uncoil from the circular storage shape, end 164 can be trapped in interior layer 120 under struts 116. This securing of end 164 reinforces/retains a compact circular shape for storing items 160.

Use of bristles in interior layer 120 also prevents lateral movement of ends 164 when stored, such that ends 164 will not slide under a different track 130. Thus, the bristles of interior layer 120 provide security for each item 160 stored such that they will not move from their stored position, and the natural force of each item 160 to unravel will not be directed anywhere except against malleable layer 118/interior layer 120. Both catheter and wire ends can be stored in the bristles of interior layer 120. Also, the different kinds of tips that wires and catheters have (angled, pigtailed, etc) is irrelevant to storage as the bristles of interior layer 120 will be able to accommodate all these shapes.

Use of heparinized saline in basin 202 can serve to moisturize items 160 as they are stored and turned in storage device 10. Heparinized saline provides anti-coagulative coating that is generally required before an item 160 is re-introduced in the patient. The use of the saline (or another liquid) as a weight also serves the need for mechanical stability of storage device 10 as items 160 are being stored and removed.

Storage device 10 may be configured in multiple sizes to suit various procedural needs. In one implementation, storage device 10 may use a single size suitable for most procedures. For example, discs 110 may be approximately 8 inches in diameter, with a three-quarter inch thickness. Struts 116 may each be about 4½ inches in length, one-half inch wide, and one-half inch deep. Each piece of malleable layer 118 may be about 3.3 inches wide (placed underneath struts 116, so as to project 1.4 inches on each side of strut 116), 4½ inches long, and three-quarters inch deep. Bristles in interior layer 120 on the underside of each piece of malleable layer 118 may be one half-inch deep. Walls 132 may extend beyond the circumference of struts 116 by about one inch. The total length of storage device 10, according to this implementation, would be about 11 inches, using considerably less table space for managing catheters and wires than in current surgical procedures.

Figure 7:
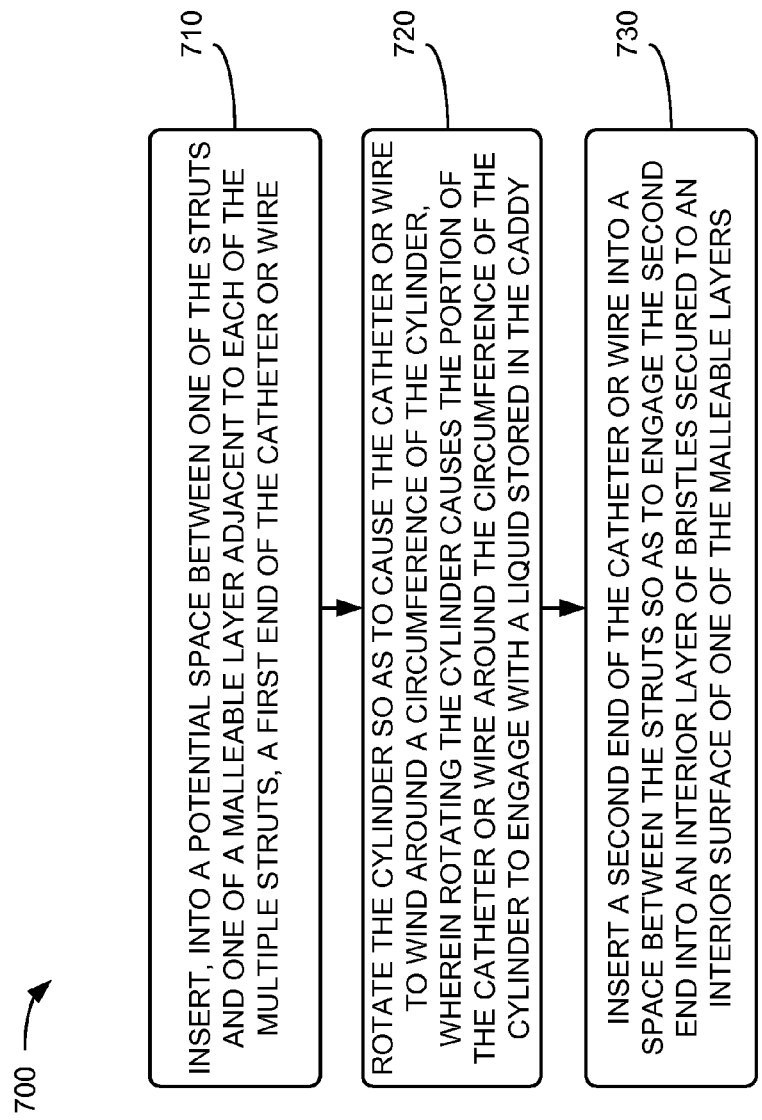
FIG. 7 is a flow diagram of a process for storing a catheter or wire on a storage device or caddy, according to an implementation described herein.

FIG. 7 is a flow diagram of an exemplary process for storing a catheter or wire on a caddy that includes a rotatable cylinder with multiple, spaced struts according to an implementation described herein. As shown in FIG. 7, process 700 may include inserting, into a potential space between one of the struts and one of a malleable layer adjacent to each of the multiple struts, a first end of the catheter or wire (block 710). For example, a technician may insert an end 162 of item 160 into potential space 119 of cylinder 100 to secure item 160 (e.g., a catheter or wire) to storage device 10.

Process 700 may further include rotating the cylinder so as to cause the catheter or wire to wind around a circumference of the cylinder, wherein rotating the cylinder causes the portion of the catheter or wire around the circumference of the cylinder to engage with a liquid stored in the caddy (block 720). For example, a technician may rotate cylinder 100 in tank 200 using crank 150. The rotation of cylinder 100 may cause item 160 to wind around the circumference of cylinder 100 within one of tracks 130. While rotating, item 160 may be circulated through liquid (e.g., a saline solution) in basin 202 of tank 200.

Process 700 may also include inserting a second end of the catheter or wire into a space between the struts so as to engage the second end into an interior layer of bristles secured to an interior surface of one of the malleable layers (block 730). For example, the technician may insert end 164 of item 160 between struts 116 and into the bristles of interior layer 120 to prevent item 160 from uncoiling around cylinder 100.

Figure 8:
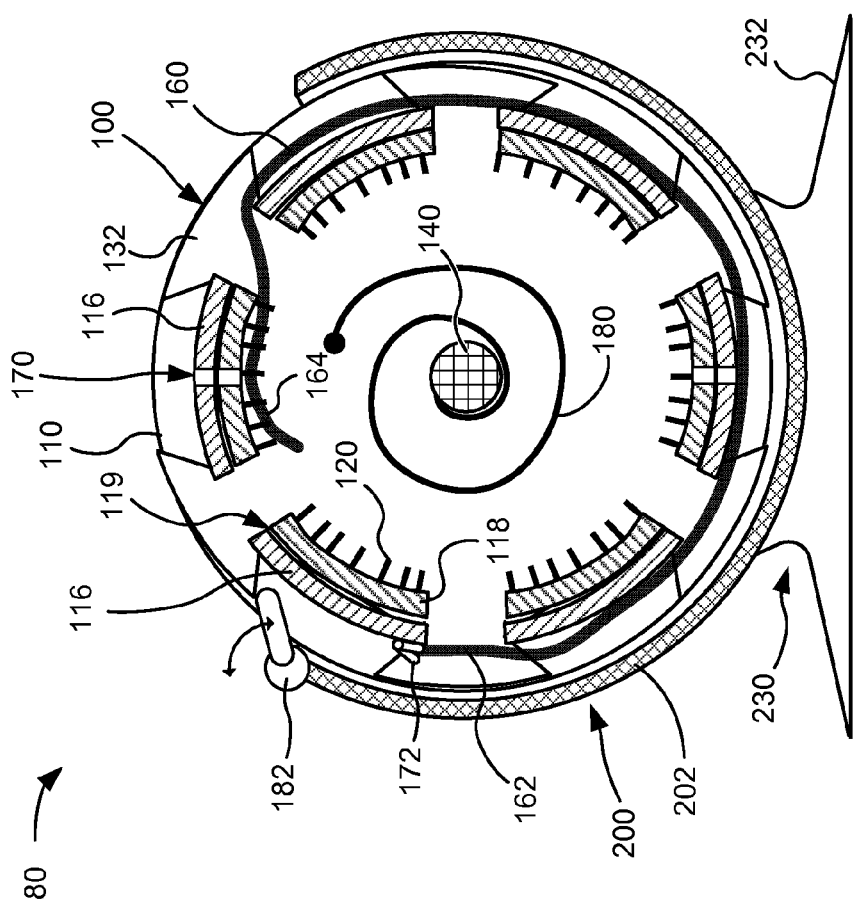
FIG. 8 is a simplified cross-sectional end view of another storage device, with a catheter or wire inserted, according to another implementation described herein.

FIG. 8 is a simplified cross-sectional end view of a storage device 80, shown with a catheter/wire inserted, according to another implementation described herein. Storage device 80 may be configured similarly to storage device 10 with a cylinder 100 and tank 200. Cylinder 100 and tank 200 may include similar components (e.g., struts 116, malleable layers 118, interior layers 120, raised walls 132, basin 202, etc.). Additionally, struts 116 and/or malleable layer 118 may include holes 170, aligned with each track 130, sized to receive the diameter of a catheter or guidewire (e.g., item 160). Thus, in this embodiment, one end (either end 162 or 164) of item 160 may be inserted into the holes and either of malleable layer 118 or interior layer 120 may be eliminated. As another example, a clip 172, latches, or other fasteners may be affixed to a portion of struts 116 and used to initially secure end 162 of item 160. Clip 172, latches, or other fasteners may hold, for example, a guidewire (e.g., one of items 160) firmly to device 80 to allow a technician to advance various catheters co-axially over the wire without requiring extra hands to hold the wire. In some implementations, clip 172, latches, or other fasteners may eliminate the need for malleable layer 118 and/or potential space 119.

In still another implementation, as shown in FIG. 8, a motor spring 180 may be included within or beside cylinder 100. Motor spring 180 may be mounted to a stationary surface (e.g., tank 200 and/or axle 140) and anchored to a rotatable surface (e.g., wall 132) so as to cause cylinder 100 to rotate and coil items (e.g., items 160) around struts 116 of cylinder 100. Other types of springs to cause rotation of cylinder 100, such as helical torsion springs or clock springs, may also be used. In one implementation, storage device 80 may include a locking mechanism 182 and/or a clutch to prevent unwanted action of the motor spring 180 and recoiling of items onto cylinder 100. Motor spring 180 may free up a technician's hand that would otherwise be required to manually rotate cylinder 100, which may be particularly useful during coiling of multiple items 160. In another implementation, a separate motor spring 180 and locking mechanism 182 may be included for each separately rotating track 130 (e.g., as described above in connection with FIGS. 1-6). In other implementations, one or more locking mechanisms 182 may be used to selectively prevent rotation of all tracks 130 or individual tracks 130, regardless of whether a motor spring 180 is included with cylinder 100.

Figure 9:
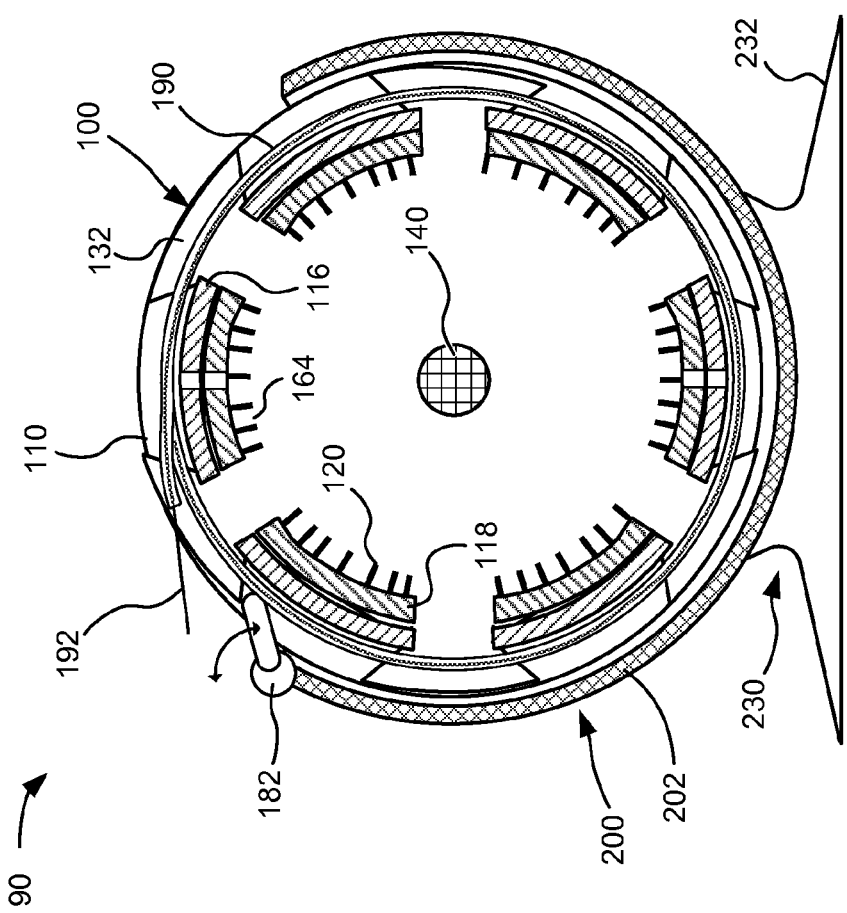
FIG. 9 is a simplified cross-sectional end view of another storage device, with a wire inserted, according to still another implementation described herein.

FIG. 9 is a simplified cross-sectional end view of a storage device 90, shown with a wire inserted, according to another implementation described herein. Storage device 90 may be configured similarly to storage devices 10 and 80 with a cylinder 100 and tank 200. Cylinder 100 and tank 200 may include similar components (e.g., struts 116, malleable layers 118, interior layers 120, raised walls 132, basin 202, etc.). Additionally, holes 170, clips 172, motor spring 180, and/or locking mechanism 182 of FIG. 8 may be used in storage device 90.

As shown in FIG. 9, a wire-holding tube 190 may be secured within a particular track 130 such that wire-holding tube 190 can rotate with cylinder 100. In one example, one or more sections of wire-holding tube 190 may be glued, tied, or clipped to an outward-facing portion of strut 116. In another example, one or more sections of wire-holding tube 190 may be glued, tied, or clipped to a side of raised wall 132. Wire-holding tube 190 may include a hollow tube sized to receive a wire 192 inserted therein. In one implementation, wire 192 may correspond to item 160. Wire-holding tube 190 may wind one or more times about a circumference of track 130 to accommodate a maximum desired length of wire 192 (e.g., 10 or more feet). When locking mechanism 182 is selectively engaged to prevent rotation of cylinder 100 (or when cylinder 100 is otherwise prevented from rotating), wire 192 may be inserted (e.g., by a technician) into wire-holding tube 190 or removed from wire-holding tube 190. Storage device 90 may include a collection of tracks 130, some with wire-holding tube 190 and some without wire-holding tube 190.

The foregoing description of exemplary implementations provides illustration and description, but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention. Therefore, the above-mentioned description is to be considered exemplary, rather than limiting, and the true scope of the invention is that defined in the following claims.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A device, comprising:
   a cylinder including:
      a first disc and a second disc,
      multiple struts arranged orthogonally between the first disc and the second disc, wherein the struts generally form a circumference with spaces between each of the struts along the circumference,
      a plurality of walls, parallel to the first disc and the second disc, wherein the walls extend through the space between the struts and beyond the circumference of the struts, and wherein the walls form a plurality of tracks around the circumference of the struts, and
      an axle extending orthogonally between the first disc and the second disc, wherein at least a portion of the cylinder rotates about the axle to wind a catheter or a wire about the circumference; and
   a tank including:
      a basin to hold a liquid solution,
      a set of opposing walls, with each wall including a notch to receive the axle so as to permit the axle to rotate within each notch while the cylinder is at least partially within the basin,
      an opening to receive the cylinder and to permit insertion of the liquid solution to the basin, and
      a base to support the tank and cylinder so as to prevent tipping during insertion and/or extraction of the catheter or wire from the cylinder,
   wherein, when the catheter or wire is wound around the cylinder, the rotation of the cylinder causes the catheter or wire to be coated in the liquid solution from the basin.

2. The device of claim 1, further comprising:
   a motor spring to cause the cylinder to rotate, wherein the motor spring provides sufficient force to cause the catheter or wire to wind around the cylinder.

3. The device of claim 1, wherein each of the struts is separated into discontinuous segments, with each segment corresponding to a width of one of the plurality of tracks, so as to permit independent rotation of each track about the axle.

4. The device of claim 1, wherein the cylinder further includes:
   a malleable layer secured to an interior surface of each of the struts, wherein the malleable layer is secured to the strut so as to form a space, to retain an end of the catheter or wire, between the malleable layer and the strut.

5. The device of claim 4, wherein, when the end of the catheter or wire is inserted into the space, rotation of the cylinder causes the catheter or wire to wind around the cylinder within one of the tracks.

6. The device of claim 4, wherein the cylinder further includes:
   an interior layer of bristles secured to an interior surface of each of the malleable layers, wherein the interior layer of bristles is configured to retain another end of the catheter or wire.

7. The device of claim 6, wherein, after the catheter or wire is wound around the cylinder, the catheter or wire is held in position by inserting the other end into the interior layer of bristles.

8. The device of claim 1, further comprising:
   a locking mechanism to selectively prevent rotation of the cylinder.

9. The device of claim 1, wherein the cylinder further includes:
   a wire-holding tube secured around one of the plurality of tracks such that wire-holding tube can rotate with the cylinder, wherein the wire-holding tube is sized to receive a wire therein.

10. A device, comprising:
    a cylinder including:
       a first disc and a second disc,
       multiple struts arranged orthogonally between the first disc and the second disc, wherein the struts generally form a circumference with spaces between each of the struts along the circumference,
       a plurality of walls, parallel to the first disc and the second disc, wherein the walls extend through the space between the struts and beyond the circumference of the struts, and wherein the walls form a plurality of tracks around the circumference of the struts, and
       an axle extending orthogonally between the first disc and the second disc, wherein at least a portion of the cylinder rotates about the axle; and
    a tank including a basin to hold a liquid solution, wherein, when a catheter or a wire is wound around the cylinder, the rotation of the cylinder causes the catheter or wire to be coated in the liquid solution from the basin.

11. The device of claim 10, wherein the tank further includes:
    a set of opposing walls, with each wall including a notch to receive the axle so as to permit the axle to rotate within each notch while the cylinder is at least partially within the basin.

12. The device of claim 11, wherein the tank further includes:
    a base to support the tank and cylinder so as to prevent tipping during insertion and/or extraction of the catheter or wire from the cylinder, wherein an interior of the base is in fluid communication with the basin such that such that the liquid solution from the basin may fill the interior of the base.

13. The device of claim 10, further comprising:
    a spring configured to cause the cylinder to rotate.

14. The device of claim 10, further comprising:
    a locking mechanism to selectively prevent rotation of the cylinder.

15. The device of claim 10, wherein each of the plurality of tracks rotate independently about the axle.

16. The device of claim 10, wherein the cylinder further comprises:
- a malleable layer secured to an interior surface of each of the struts, wherein the malleable layer is secured to the strut so as to form a space, to retain an end of the catheter or wire, between the malleable layer and the strut, and
- an interior layer of bristles secured to an interior surface of each of the malleable layers, wherein the interior layer of bristles is configured to retain another end of the catheter or wire.

17. The device of claim 16, wherein, when the end of the catheter or wire is inserted into the space, rotation of the cylinder causes the catheter or wire to wind around the cylinder within one of the tracks, and
- wherein, after the catheter or wire is wound around the cylinder, the catheter or wire is held in position by inserting the other end into the interior layer of bristles.

18. The device of claim 10, wherein the cylinder further includes:
- a wire-holding tube secured around one of the plurality of tracks such that wire-holding tube can rotate with the cylinder.

* * * * *